United States Patent [19]

Zimmerman et al.

[11] Patent Number: 4,493,699

[45] Date of Patent: * Jan. 15, 1985

[54] CONTRACEPTIVE METHODS

[75] Inventors: Ronald E. Zimmerman, Danville; Philip J. Burck, Indianapolis; C. David Jones, Indianapolis; Arvind L. Thakkar, Indianapolis, all of Ind.

[73] Assignee: Eli Lilly and Company, Indianapolis, Ind.

[*] Notice: The portion of the term of this patent subsequent to Apr. 28, 1998 has been disclaimed.

[21] Appl. No.: 366,889

[22] Filed: Apr. 8, 1982

[51] Int. Cl.³ ............................................. A61K 9/02
[52] U.S. Cl. ...................................... 604/55; 604/892
[58] Field of Search .......................... 128/127–131; 604/904, 892, 369, 55; 424/15, 19, 22, 28

[56] References Cited

U.S. PATENT DOCUMENTS

| 4,012,496 | 3/1977 | Schopflin et al. | 128/130 |
| 4,067,961 | 1/1978 | Laughlin | 424/15 |
| 4,264,575 | 4/1981 | Zimmerman et al. | 424/22 |
| 4,264,576 | 4/1981 | Zimmerman et al. | 424/22 |
| 4,264,577 | 4/1981 | Zimmerman et al. | 424/22 |
| 4,309,997 | 1/1982 | Donald | 604/369 |

*Primary Examiner*—C. Fred Rosenbaum
*Assistant Examiner*—Sherri E. Vinyard
*Attorney, Agent, or Firm*—James L. Rowe; Arthur R. Whale

[57] ABSTRACT

Long chain alkyl and alkenyl sulfonates, sulfates and sulfoalkyl alkanoate salts, administered intravaginally for contraception.

9 Claims, No Drawings

CONTRACEPTIVE METHODS

This invention relates to improved methods and compositions useful in human and veterinary medicine for the control of fertility.

Contraceptive methods involving the administration of chemical substances are widely practiced among women who desire to limit pregnancies. Such methods control fertility through various biological mechanisms. Among the presently used chemical methods of fertility control, the most important are those which act by means of the following: (a) suppression of ovulation through inhibition of gonadotropin release; (b) alteration of the female reproductive tract to prevent migration of sperm to the site of fertilization or, if fertilization occurs, to block implantation of the zygote (nidation); or (c) spermicidal action.

The oral contraceptives are the most prominent chemical contraceptive agents. These agents are of two types: (a) an estrogen combined with a progestin, and (b) a progestin alone. The contraceptives of the combined type act primarily by suppressing ovulation by negative feedback to prevent gonadotropin (LH and FSH) release by the hypothalamus, but alterations in the reproductive tract may also contribute to the antifertility effect. Such alterations include changes in the cervical mucus (which increase the difficulty of sperm migration) and in the endometrium (which decrease the likelihood of nidation). The action of a progestin alone in a very low oral dose (the "mini-pill") appears to involve primarily alterations in the female reproductive tract, but ovulation suppression may also occur. Although the oral contraceptives are highly effective, their use is associated with unpleasant side effects (such as nausea, depression, weight-gain, and headache) plus an increased long-term risk of severe disease (such as thromboembolism, stroke, myocardial infarction, hepatic adenoma, gall bladder disease, and hypertension). Bleeding irregularities (such as breakthrough bleeding, spotting, and amenorrhea) are also frequent. A progestin, when administered alone, may cause an increased incidence of changes in menstrual patterns, especially a marked increase in the amount and duration of menstrual bleeding.

Besides the oral route of administration a progestin alone may be administered systemically by various sustained-release dosage forms which include: (a) depo injection (IM) of an insoluble progestin (e.g. medroxy progesterone acetate), (b) a subdermal implant, or (c) an intravaginal insert. With these methods of administration, the progestin is absorbed into the body continuously at a very low daily dose, and the systemic effects are similar to those produced by oral administration of a progestin. However, as with the oral progestins, the sustained release methods may cause serious menstrual flow irregularities.

A recently introduced method of contraception involves the sustained release of progesterone locally within the uterine lumen. In this method, the progesterone is incorporated into a chamber within a flexible intrauterine devic (IUD) formed from a polymer which is capable of releasing progesterone continuously into the uterine fluids at a slow rate over a prolonged period of time. The progesterone acts primarily locally to produce progestational alterations in the cervical mucus and endometrium. However, the antifertility action may also be caused by the reaction of the endometrium to the device itself ("IUD effect") or by systemic absorption of progesterone through the uterine membrane. Again, as with other progestin-only therapies, there is an increased incidence of menstrual flow irregularities. Another disadvantage of this method, is the increased risk of ectopic pregnancy.

Another recent development is the flexible IUD bearing metallic copper. The contraceptive action of this device results from the combined effects of the copper (which very slowly dissolves in the uterine fluids), which acts on the blastocyst and on the cervical mucus or endometrium, and of the IUD itself, which causes a foreign body reaction in the endometrium.

Other chemical methods of contraception include the post coital administration of estrogens (e.g. diethylstilbestrol or ethynylestradiol) which act to prevent nidation or of prostaglandins which act as abortifacients. Both of these methods, at present, are limited to emergency situations. Still in the very early stages of development are immunological methods (vaccination) and methods involving the direct control of LHRH secretion from the pituitary by LHRH agonists or antagonists.

Another group of chemical contraceptive agents are the local spermicides, such as nonoxynol or octoxynol, which are placed into the vagina immediately prior to coitus in the form of creams, foams, jellies, or suppositories. The spermicidal action takes place either in the vagina or elsewhere in the reproductive tract. For the latter to occur, the spermicidal agent is either adsorbed on sperm membranes or is transported into the uterus under the influence of uterine contractions. The spermidical methods are not altogether reliable in preventing pregnancy and are inconvenient to use.

The intrauterine device (IUD) is the most common alternative to the use of oral contraceptives. The antifertility effect of the IUD is not caused by chemical activity. Instead the material forming the IUD induces a foreign body reaction (irritation) in the contiguous endometrium which appears to interfere in some way with nidation. The use of the IUD is complicated, however, by serious side effects including the possibility of uterine perforation, pelvic inflammation, discomfort, or aggravated menstrual periods.

From the foregoing brief summary, it is evident that the presently available methods of contraception are inadequate for various reasons: (a) they may produce unpleasant side effects or increase the risk of serious disease, (b) they may be unreliable, or (c) they may be inconvenient and intrude on sexual enjoyment. Although many women practice contraception in spite of these inadequacies, a need exists for improved contraceptive methods which combine effectiveness with increased safety and convenience. It is an object of this in invention to provide such an improved method.

BACKGROUND OF THE INVENTION

The alkyl or alkenyl sulfate salts have surface-active properties, and the sodium salts of dodecyl sulfate (lauryl sulfate), tetradecyl sulfate (myristyl sulfate), and hexadecyl sulfate (cetyl sulfate) are particularly useful surfactants for many applications. Sodium lauryl sulfate, for example, is widely used in topical creams, lotions and other preparations used for pharmaceutical or cosmetic purposes. A mixture of sodium lauryl sulfate and sodium myristyl sulfate is used commercially as a wetting agent, primarily in the paper industry. It is well known that surfactants may denature proteins when present in aqueous solutions in sufficient concentrations because the surface activity may affect peptide conformation. Sodium n-tetradecyl sulfate does not show classical spermicidal activity in standard in vitro tests which measure the ability of the compounds to kill or immobilize sperm.

The straight chain $C_{11-16}$ alkylsulfonates are available commercially in the form of the sodium salt, which are preferred for the purposes of this invention. Other salts can be prepared by methods well-known in the art.

DESCRIPTION OF THE INVENTION

This invention provides a contraceptive method in which a class of alkyl or alkenyl sulfates or alkyl sulfonate or alkyl or alkenyl sulfoalkylalkanoate salts (to be more fully described below) will effectively prevent fertilization when introduced in very small amounts in the mammalian vagina prior to coitus. The alkyl or alkenyl sulfate salts, the alkyl sulfonate salts and the alkyl or alkenyl sulfoalkylalkanoate salts are non-hormonal, and, hence, offer significant advantages over the oral contraceptive steroids and the sustained release progestin compositions heretofore used. The antifertility effect of each of these classes of salts can be demonstrated in female rabbits using standard pharmacological test procedures whereby the test compound is introduced locally within the vagina of the animal, the animal is then bred to a fertile buck, and the genital system is then examined to determine the number of embryos.

The alkyl or alkenyl sulfate, alkyl sulfonate or alkyl or alkenyl sulfoalkylalkanoate salts can be delivered satisfactorily either by direct application of a formulation such as a suppository, sponge or jelly or by slow release from a polyurethane composition. Administration of an alkyl or alkenyl sulfate alkyl sulfonate or alkyl or alkenyl sulfoalkylalkanoate salt in the female reproductive tract by means of a sustained release polyurethane composition provides a convenient and acceptable method of contraception and is preferred over administration of a contraceptive jelly or sponge.

To summarize, this invention provides a method of contraception in a female mammal which comprises introducing within the vaginal cavity of said female, just prior to coitus but preferably continuously at a controlled rate over a prolonged period of time, an effective amount of an alkyl sulfate salt of the formula:

$$R-OSO_3-M \qquad \qquad I$$

wherein R is:

(a) $C_{11}-C_{30}$ straight chain alkyl or alkenyl;

(b) $C_{10}-C_{30}$ branched chain alkyl or alkenyl, the α-carbon of which is not branched; or (c) $C_{13}-C_{30}$ branched chain alkyl or alkenyl, the α-carbon of which is branched;

or of an alkyl or alkenyl sulfoalkylalkanoate salt of the formula:

$$R^2-\overset{O}{\underset{\|}{C}}O-(CH_2)_nSO_3M \qquad \qquad II$$

wherein $R^2$ is alkenyl or straight chain alkyl of from 9-13 carbon atoms or a branched chain alkyl of from 9-17 carbon atoms, and n is 2, 3 or 4;
or of an alkylsulfonate of the formula $$R^1SO_3M \qquad \qquad III$$

wherein $R^1$ is straight or branched alkyl of from 11-16 carbon atoms; and M is a pharmaceutically acceptable non-toxic cation.

As employed herein and in the claims, the term "α-carbon" denotes the carbon atom of the alkyl or alkenyl group (R, $R^1$, $R^2$) which is bonded to the sulfate or sulfonate or sulfoalkylalkanoate function.

When the "α-carbon" is not branched, a grouping of the following structure is present, using the sulfate function and an alkyl radical for exemplary purposes only, $$alkyl-CH_2-OSO_3M$$

When the α-carbon is branched, a grouping of this structure

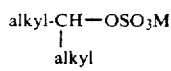

or of this structure

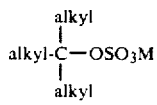

is present.

It will be also understood that when the α-carbon is branched, further branching may occur at other carbon atoms of the alkyl or alkenyl group. As employed herein and in the claims, the term "alkenyl" means an unsaturated branched chain or straight chain univalent hydrocarbon radical which may contain one or two double bonds. The double bonds may be oriented in either the cis or trans configuration. As will be apparent to one skilled in the art, the double bond cannot be located in the alkenyl chain at either the α-carbon or β-carbon relative to the sulfate, sulfonate or sulfoalkylalkanoate function. Moreover, the alkenyl group may contain two or more double bonds.

Illustrative alkyl groups which R can represent include:

Straight chain alkyl groups of the formula:

$$CH_3(CH_2)_n-$$

wherein n is an integer from 10 to 29 (preferably 10 to 20); for example: n-undecyl, n-dodecyl, n-tridecyl, n-tetradecyl, n-pentadecyl, n-hexadecyl, n-heptadecyl, n-octadecyl, n-nonadecyl, n-eicosyl, and the like.

α-Branched chain alkyl groups of the formula:

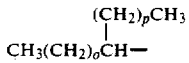

wherein o and p are, independently, integers from 0 to 27, provided that o+p must be no less than 7 and no greater than 27; for example:

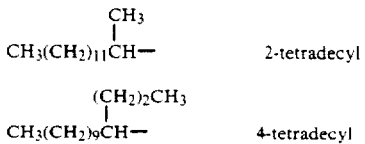

-continued $$CH_3(CH_2)_7\overset{(CH_2)_4CH_3}{\underset{|}{CH}}-  \quad \text{6-tetradecyl}$$

$$CH_3(CH_2)_6\overset{(CH_2)_5CH_3}{\underset{|}{CH}}-  \quad \text{7-tetradecyl}$$

$$CH_3(CH_2)_8\overset{(CH_2)_5CH_3}{\underset{|}{CH}}-  \quad \text{7-hexadecyl}$$

$$CH_3(CH_2)_7\overset{(CH_2)_6CH_3}{\underset{|}{CH}}-  \quad \text{8-hexadecyl}$$

$$CH_3(CH_2)_8\overset{(CH_2)_7CH_3}{\underset{|}{CH}}-  \quad \text{9-octadecyl.}$$

Alkyl groups not branched at the α-carbon, of the formula:

$$CH_3(CH_2)_q\overset{CH_3}{\underset{|}{CH}}(CH_2)_rCH_2- \quad (a)$$

wherein r and q are, independently, integers from 0 to 26, provided that r+q must be no less than 6 and no greater than 26; for example:

$$CH_3\overset{CH_3}{\underset{|}{CH}}(CH_2)_{11}- \quad \text{12-methyltridecyl;}$$

$$CH_3\overset{CH_3}{\underset{|}{CH}}(CH_2)_a\overset{CH_3}{\underset{|}{CH}}(CH_2)_b- \quad (b)$$

wherein a and b are, independently, integers from 1 to 24, provided that a+b must be no less than 5 and no greater than 25; for example:

$$CH_3\overset{CH_3}{\underset{|}{CH}}(CH_2)_3\overset{CH_3}{\underset{|}{CH}}CH_2CH_2 \quad \text{tetrahydrogeranyl;}$$

$$CH_3\overset{CH_3}{\underset{|}{CH}}(CH_2)_c\overset{CH_3}{\underset{|}{CH}}(CH_2)_d\overset{CH_3}{\underset{|}{CH}}(CH_2)_e- \quad (c)$$

wherein c, d, and e are, independently, integers from 1 to 21, provided that c+d+e must be no greater than 23; for example:

$$CH_3\overset{CH_3}{\underset{|}{CH}}(CH_2)_3\overset{CH_3}{\underset{|}{CH}}(CH_2)_3\overset{CH_3}{\underset{|}{CH}}(CH_2)_2 \quad \text{3,7,11-trimethyldodecyl; or}$$

$$CH_3(CH_2)_f\overset{(CH_2)_gCH_3}{\underset{|}{CH}}CH_2- \quad (d)$$

wherein f and g are, independently, integers from 0 to 26, provided that g+f must be no less than 6 and no greater than 26; for example:

$$CH_3(CH_2)_4\overset{(CH_2)_7CH_3}{\underset{|}{CH}}CH_2- \quad \text{2-octyldodecyl.}$$

Illustrative alkenyl groups which R represents include:

Monounsaturated straight chain alkenyl groups of the formula:

$$CH_3(CH_2)_tCH=CH(CH_2)_sCH_2-$$

wherein t is an integer from 0 to 25 and s is an integer from 1 to 26, provided that t+s must be no less than 7 and no greater than 26; for example:

| | |
|---|---|
| cis-$CH_3(CH_2)_3CH=CH(CH_2)_8-$ | myristoleyl |
| trans-$CH_3(CH_2)_3CH=CH(CH_2)_8-$ | myristeladyl |
| cis-$CH_3(CH_2)_7CH=CH(CH_2)_8-$ | oleyl |
| trans-$CH_3(CH_2)_7CH=CH(CH_2)_8-$ | elaidyl |

Di-unsaturated straight chain alkenyl groups of the formula:

$$CH_3(CH_2)_xCH=CH(CH_2)_yCH=CH-(CH_2)_zCH_2-$$

wherein x is an integer from 0 to 22 and y and z are, independently, each an integer from 1 to 23, provided x+y+z must be no less than 5 and no greater than 24; for example:

cis,cis—$CH_3(CH_2)_4CH=CHCH_2CH=CH(CH_2)_8$—linoleyl Monounsaturated branched chain alkenyl groups of the formula:

$$CH_3\overset{CH_3}{\underset{|}{CH}}-(CH_2)_wCH=CH-(CH_2)_u-CH_2$$

wherein w is an integer from 0 to 23 and u is an integer from 1 to 24, provided that w+u must be no less than 4 and no greater than 24; for example:

$$CH_3\overset{CH_3}{\underset{|}{CH}}CH_2CH=CH(CH_2)_8 \quad \text{13-methyltridec-9-enyl}$$

The alkyl or alkenyl sulfate salts of the formula R—$OSO_3$—M, wherein R and M have the meanings hereinabove defined, are either known compounds, or they can be made from known compounds by known reactions or by modifications thereof which will be obvious to those skilled in the art. Some are available commercially.

One method for preparing the alkyl or alkenyl sulfates employed in this invention is by treating the appropriate alkanol or alkenol (R-OH) with chlorosulfonic acid in a non-reactive organic solvent (e.g. hexane or tetrahydrofuran). The reaction can be carried out at room temperature or with mild heating (to about 50°), or it can be carried out at low temperatures (to −25° C.) to prevent side reaction with sensitive starting materials. The product is reacted with a suitable base in order to obtain the particular cation salt which is desired.

Another method for preparing the alkyl or alkenyl sulfate salts is by reacting the appropriate alkanol or alkenol with "pyridine-sulfur trioxide complex" in the presence of pyridine and acetic anhydride in a non reactive solvent (e.g. toluene). The reaction is carried out, preferably, at an elevated temperature (e.g. 80° to 150° C.). The product of the reaction forms as the pyridinium salt, but other salts can be formed by treating the pyridinium salt with a suitable base, such as potassium hydroxide, sodium hydroxide, lithium hydroxide, calcium hydroxide, magnesium hydroxide, etc.

The $C_{11}-C_{16}$ straight chain alkyl group represented by $R^1$ above include the following: undecyl, dodecyl, tridecyl, tetradecyl, pentadecyl, hexadecyl.

The $C_{11}-C_{16}$ straight-chain alkyl sulfonates represented by III above are available commercially, usually in the form of their sodium salts. Other salts can be made by processes well known to the art.

The sodium sulfoalkyl alkanoates of Formula II, when n is 3 or 4, are prepared by reacting an appropriate sodium alkanoate ($R^2CO_2Na$) with propane sultone or butane sultone in an inert organic solvent according to the procedure of T. Hikota, *Bulletin of the Chemical Society of Japan*, 43, 2236 (1970). The compounds of Formula II, wherein n is 2, are prepared by treating an alkanoic acid chloride ($R^2COCl$) with sodium isethionate also by the procedure of Hikota supra. The alkanoic acids employed as starting materials, and the sodium salts thereof, are either known compounds or can be prepared from known compounds by methods well known in the art.

Examples of straight chain alkanoate compounds useful for the purpose of this invention are:

sodium sulfopropyl decanoate ($R^2$ is $C_9$ alkyl; n is 3; M is sodium);

sodium sulfopropyl undecanoate ($R^2$ is $C_{10}$ alkyl; n is 3; M is sodium);

sodium sulfopropyl dodecanoate ($R^2$ is $C_{11}$ alkyl; n is 3; M is sodium);

sodium sulfopropyl tridecanoate ($R^2$ is $C_{12}$ alkyl; n is 3; M is sodium); and sodium sulfopropyl tetradecanoate ($R^2$ is $C_{13}$ alkyl; n is 3; M is sodium);

sodium sulfoethyl dodecanoate ($R^2$ is $C_{11}$ alkyl; n is 2; M is sodium).

When $R^2$ is a branched chain alkyl group, the preferred alkyl groups are those which have the formula:

$$CH_3-(CH_2)_m-\overset{CH_3}{\underset{|}{CH}}-(CH_2)_{m'}-$$

wherein m and m' are, independently, an integer from 0 to 14, provided that m+m' must be no less than 6 or no greater than 14. Examples of branched chain alkanoate compounds useful for the purpose of this invention are:

sodium sulfopropyl 12-methyltridecanoate

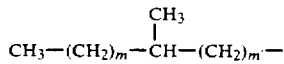

($R^2$ is $CH_3CH(CH_2)_{10}-$;

n is 3; M is sodium);

sodium sulfopropyl 15-methylheptadecanoate

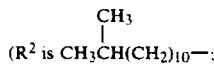

($R^2$ is $CH_3CH_2CH(CH_2)_{14}-$;

n is 3; m is sodium);

sodium sulfopropyl 16-methylheptadecanoate

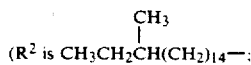

($R^2$ is $CH_3CH(CH_2)_{15}-$;

n is 3; M is sodium);

When $R^2$ is an alkenyl group, the preferred alkenyl groups are those of the formula

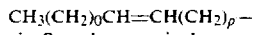

$CH_3(CH_2)_oCH=CH(CH_2)_p-$ wherein 0 and p are, independently, an integer from 0 to 10, provided that 0+p must be no less than 6 or no greater than 10. Examples of straight chain alkenoate compounds useful for the purpose of this invention are:

sodium sulfopropyl myristoleate ($R^2$ is cis-$CH_3(CH_2)_3CH=CH(CH_2)_7-$, n is 3; M is sodium)

sodium sulfopropyl myristelaidate ($R^2$ is trans-$CH_3(CH_2)_3CH=CH-(CH_2)_7-$; n is 3; M is sodium).

The cation (M) of the compounds of the above formulas (I, II and III) can be any pharmaceutically acceptable, non toxic cation such as sodium, potassium, lithium, calcium, magnesium, copper, aluminum, pyridinium, substituted pyridinium, zinc, ammonium, or substituted ammonium, e.g. diethanolammonium or triethanolammonium. It will be appreciated by those skilled in the art that when the cation (M) has a valency greater than one, more than one anionic moiety will be associated with the cation.

The alkyl or alkenyl sulfate, sulfonate and sulfoalkylalkanoates salts represented by the above formulas I, II and III control fertility by inhibiting enzymes which are required during fertilization to allow sperm to penetrate the outer investments of the ovum. An ovum contains three outer investments (the cumulus oophorus, the corona radiata, and the zona pellucida) which are barriers to fertilization. In the male, and when first deposited in the female, sperm is incapable of fertilizing an ovum since it lacks the capacity to penetrate the outer investments. Before fertilization can occur, specific hydrolytic enzymes emanating from the sperm must digest each investment so as to form a passage for sperm penetration. The process by which sperm achieve the ability to penetrate the ovum is known as "capacitation". Capacitation involves activation of the ovum penetrating enzymes needed to attack each investment. There is evidence that the activation of the ovum penetrating enzymes may involve the removal of specific inhibitors of the enzymes. The exact biochemical transformations occurring during capacitation are not fully understood, but the enyzmes must exert their action either while bound to the sperm membranes or upon release from sperm after the sperm and the ovum make contact in the fallopian tube. For a review of the biochemistry of capacitation and of the inhibition of ovum penetrating enzymes see McRorie et al., *Ann. Rev. Biochem.*, 43, 777 (1974) and E. S. Hafez, Ed., "Human Semen and Fertility Regulation in Men", C. V. Mosby Co., St. Louis, Mo., 1976, pages 201 to 242 and 563 to 582.

It is believed that the alkyl or alkenyl sulfate, sulfonate and sulfoalkylalkanoate salts as used in our novel methods inhibit in vitro the action of hyaluronidase and/or acrosin, the sperm acrosomal enzymes which are known to be responsible in vivo for the penetration of the cumulus oophorus and the zona pellucida, respectfully. Hyaluronidase is a glycosidase which causes degradation of the hyaluronic acid which occurs between the cells of the cumulus oophorus. Acrosin is a proteinase which causes degradation of the glycoproteins of the zona pellucida. Inhibition of each of these enyzmes in vivo will lead to interruption of the ovum penetration process thereby effectively preventing fertilization and pregnancy. The inhibition of hyaluronidase (from bull testes) in vitro by $C_{12}-C_{14}$ alkyl sulfate sodium salts is described by M. Mathews, *J. Am. Chem. Soc.*, 76, 2948 (1954).

The ability of sodium n-tetradecyl sulfate, a compound coming within the scope of formula I above, to prevent digestion of the cumulus oophorus and/or the zona pellucida has been demonstrated in in vitro tests wherein an isolated ovum from a rabbit is observed under a microscope while being incubated in calcium-free Ringer's solution in the presence of testicular hyaluronidase or acrosin with and without sodium n-tetradecyl sulfate being present in the medium. In the absence of sodium n-tetradecyl sulfate, complete removal of the cumulus oophorus and zona pellucida is observed. With sodium n-tetradecyl sulfate present, the cumulus oophorus and zona pellucida remain substantially intact.

In order to prevent pregnancy, an effective, amount of the alkyl or alkenyl sulfate, sulfonate or sulfoalkylalkanoate salt must be present at the site of fertilization in the fallopian tube when sperm and the ovum make contact prior to penetration of the ovum. The alkyl or alkenyl sulfate, sulfonate or sulfoalkyl alkanoate salt can be administered by introduction locally within the vaginal cavity. By this mode of administration, the salt is carried to the site of fertilization either by adsorbtion onto sperm membranes or by transport in vaginal fluids. In vaginal fluids, the compound passes to the uterine fluids either adsorbed on sperm membranes or by active transport under the influence of uterine contractions. The preferred method of administration from the standpoint of convenience to the female user is to introduce the alkyl or alkenyl sulfate, sulfonate or sulfoalkylalkanoate salt continously within the vagina during the fertile period of the female (i.e. the period three to four days after ovulation when an ovum is present in the fallopian tube). By this method, an effective amount of the active compound is present within the vagina each day to prevent fertilization if coitus should occur during the fertile period. Such a contraceptive method is independent of the sex act and avoids the inconvenience of repeated independent dosages.

The continuous administration of the active compound which is preferred can be accomplished effectively by incorporating it into a polyurethane composition and placing said composition retentively in the vaginal cavity. The active compound is slowly introduced into the vaginal fluids by release from the polyurethane at a controlled rate, an effective amount of the compound being present continuously in such fluids. The polyurethane acts as an insoluble, non-irritating carrier matrix for supporting the active compound while it is being introduced into the vaginal fluids. Polyurethane is bioinsoluble and biocompatible (i.e. it is non-toxic, insoluble, and physiologically inert when in contact with body tissues and fluids). The polyurethane carrier can be formed in a shape and size suitable for insertion and comfortable retention in the vaginal cavity. For intravaginal use, the polyurethane can be formed as a flexible ring, similar in configuration to that of the retaining ring of a diaphragm, which is known in the art to be useful for retention in the vagina. [See, U.S. Pat. Nos. 3,545,439 and 3,920,805.]

These flexible rings containing a contraceptive material comprising a long chain aliphatic sulfate or sulfonate or sulfoalkylalkanoate salt can be prepared by different methods. We prefer to use the following procedure, employing sodium n-tetradecyl-sulfate as the contraceptive agent for exemplary purposes only: A given weight of a segmented polyurethane (a polyether based polyurethane manufactured under the trademark Estane 5714 by the B. F. Goodrich Company, Specialty Polymers and Chemical Div., 6100 Oak Tree Boulevard, Cleveland, OH, 44131 and approved for intravaginal use by The Food and Drug Administration) was dissolved in THF. An equal weight of sodium n-tetradecylsulfate was added to form a slurry. The slurry was cast into thin films, each film cut into small pieces and the pieces dried in a vacuum oven at about 70° C. The drug-polyurethane blend pieces were then loaded into the feed section of an injection molding machine (Frohring Mini-jector-Model 45 sold by Newbury Industries, Inc., Newbury, OH) equipped with a mold for a human size vaginal ring (2.244" OD×1.536" I.D. cavity). The drug-urethane blend was equilibrated at 130° C. temperature and then forced under pressure into the mold cavities (barrel and nozzle temperatures were 130° C.). The rings thus produced were annealed by placing over a pipe of slightly smaller diameter (1.5") than the I.D. of the ring to prevent shrinkage. Annealing was carried out in an air circulating oven at 45° C. for 30 minutes.

Drug-polyurethane rings prepared as above release large amounts of drug when first placed in contact with vaginal or other fluids. In order to diminish the initial burst of drug (3–4 times amount of drug released day 1 compared to days 2–10) and to give a constant release rate of drug in contraceptive concentration for a 21 day period, the molded rings were coated with Estane or similar polymer by dipping repeatedly in a DMF solution containing 12% (w/w) Estane 5714. Solvent was allowed to evaporate for 1 hour between dips. Coated rings were prepared with the ratio of radius of the coated ring to the ring itself varying from 1.02 to 3.29. Studies of drug release rates indicated that thinner coatings (ratio 1.02–1.06) yielded the desired drug delivery rate. Vaginal rings prepared as above released the contraceptive agent into the vaginal fluids at a constant rate sufficient to provide a contraceptive concentration of the drug for 20 days.

Although the vaginal device prepared above contained 50% drug, similar devices containing 18–25% drug were prepared in similar fashion, and gave constant drug release.

Vaginal rings of a size suitable for insertion into rabbit vaginas were prepared as above with the cavities in the injection molds being 0.878" O.D.×0.473" I.D. These rings were coated without annealing with 100–150μ layers of Estane 5714.

The in vivo testing of rings thus fabricated was carried out as follows: the ring was placed in 50 ml. of water at 37° C. and assayed 2–3 times daily for release of sodium n-tetradecylsulfate. When the release rate exceeded 500/mcg./day, the rings were sutured into the vaginas of five Dutch belted does. After recovery from surgery, the does were bred to bucks of proven fertility weekly for four weeks. Ten days after the last breeding, the does were sacrificed and their uteri examined for embryos. None of the does were pregnant.

It is desirable that the rate of delivery of the active drug be substantially constant over the period in which the carrier composition is present in the vaginal cavity. Preferably the duration of drug delivery should cover the fertile period of the female. The duration of release should be ideally about one month. The carrier composition can then be removed at the start of the menstrual period and re-inserted after bleeding stops. However, as long as an effective amount of the active compound can be released into the vaginal fluids, the intravaginal composition can be inserted prior to coitus and removed shortly thereafter, rather than allowing the composition to be retained in the vagina for a longer duration of time.

Release rates of from 0.5 to 10 mg. per day of sulfonate, sulfate or sulfoalkyl alkanoates salts are desirable when utilizing intravaginal devices such as that illustrated above.

For administration to females, who for personal reasons do not wish to use a sustained release medicated intrauterine or intravaginal composition, an alternative method of administration of the active compound is by means of a pharmaceutically acceptable jelly, foam, cream, suppository, or sponge which is inserted into the vagina immediately prior to coitus in a manner similar to that employed for administering conventional spermicidal compositions. [See the article entitled "Spermicides", *Population Reports;* Series H, Vol. 7, No. 5, Sept., 1979; published by Population Information Program, The Johns Hopkins University, Baltimore, Md.] The jelly, foam, cream, suppository or sponge acts as a vehicle for carrying an effective amount of the active ingredient into the vaginal fluids from where it is carried into the uterus by adsorption on sperm membranes or by active transport. The active ingredient can be compounded into vaginal jellies, foams, creams, suppositories or sponges according to procedures which are conventional in the art, by employing the usual excipients (buffers, emulsifiers, preservatives, and the like), the choice and amount of which will be apparent to those skilled in the art.

For reasons of convenience, esthetics, and more precise control of dosage, a vaginal suppository is preferred. The suppository composition must be chemically and physically stable under conditions of storage and handling, and also must be capable of melting and-/or dissolving when inserted in the vagina to effect satisfactory release of the active compound into the vaginal fluids. A preferred suppository composition comprises an effective amount of the active compound in a suitable polyethylene glycol vehicle. Various polyethylene glycols, either alone or in combination, are known in the art to be useful for making vaginal suppository composition, and the choice of a particular vehicle will be apparent to those skilled in the art.

In employing a sponge as a carrier for our contraceptive substances, an effective amount of the active compound can be absorbed into a biocompatible, bioinsoluble, non-toxic sponge-like soft natural or synthetic polymer or polymer-like substance such as collagen. The sponges, when inserted and retained in the vagina, will release the compound by desorption into the vaginal fluids. The sponge can be allowed to remain in the vagina during coitus or it can be removed prior to coitus. Suitable polymers for this use are well known in the art, for example, a hydrophilic polymer, such as polymeric 2-hydroxyethyl methacrylate which, if desired, may contain a cross-linking agent (e.g. dimethacrylate).

The intravaginal method of this invention employing a jelly vehicle for placing the contraceptive drug in the vagina prior to coitus is illustrated by the following examples.

Equal volumes of K-Y-jelly ® and either Ca++ free Ringer's solution or a 10 mg./ml. solution of the compound to be tested in Ca++ free Ringer's solution are well mixed. One milliliter of this mixture is placed in the vagina of a virgin Dutch belted rabbit using a syringe. The female is then immediately bred to a fertile buck. The female is injected I.V. with 100μ of human chorionic gonadotrophin to assure a good ovulation rate.

After approximately 14 days the females are sacrificed by cervical dislocation and the genital system examined for embryos.

When tested as above described sodium n-tetradecyl sulfate, sodium sulfopropyl n-dodecanoate and sodium n-tetradecylsulfonate gave the results shown below in Table I:

TABLE I

Inhibition of fertilization by acrosin inhibitors in rabbits by intravaginal administration

| Name of Compound | Treatment | No. of animals | No. of embryos | Avg. No. of Embryos per animal |
|---|---|---|---|---|
| Sodium n-tetradecyl sulfate | control | 5 | 13 | 2.6 |
| | treated | 4 | 0 | 0 |
| Sodium n-tetradecyl sulfonate | control | 5 | 16 | 3.2 |
| | treated | 5 | 13* | 2.6 |
| Sodium sulfopropyl n-dodecanoate | control | 4 | 31 | 7.7 |
| | treated | 6 | 0 | 0 |

*one female had 9 embryos

Suppositories weighing 100 mg. are made to contain 1 mg. of sodium n-tetradecyl sulfate in a vehicle consisting of 35% polyethylene glycol 400, 35% polyethylene glycol 1540, and 30% polyethylene glycol 4000. A suppository is placed in the vagina of each of six female Dutch belted rabbits. Fifteen minutes later, each rabbit is bred to a buck of proven fertility and is also injected with 100 I.U. of human chorionic gonadotropin. Each of six control animals are similarly treated using identical 100 mg. suppositories made from the same vehicle without the active contraceptive. The animals are sacrificed after 12 days and are examined for embryos. The results are shown below in Table II.

TABLE II

| Treatment | No. of Animals | Total No. of Embryos | Embryos Per Animal ($\bar{x}$ + std. dev.) |
|---|---|---|---|
| sodium n-tetradecyl sulfate | 6 | 3 | 0.5 ± 1.2 |
| control | 6 | 23 | 3.83 ± 3.6 |

We claim:

1. A method of contraception in a female mammal which comprises continuously introducing within the vaginal cavity of said female, over a prolonged period of time at a controlled rate, a contraceptively effective amount of an alkyl or alkenyl sulfate salt of the formula:

$$R-OSO_3-M$$

wherein R is:
(a) $C_{11}-C_{30}$ straight chain alkyl or alkenyl;
(b) $C_{10}-C_{30}$ branched chain alkyl or alkenyl, the α-carbon of which is not branched; or
(c) $C_{13}-C_{30}$ branched chain alkyl or alkenyl, the α-carbon of which is branched;

or of an alkyl or alkenyl sulfoalkylalkanoate salt of the formula

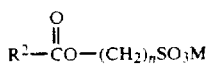

wherein $R^2$ is alkenyl or straight chain alkyl of from 9–13 carbon atoms or a branched chain alkyl of from 9–17 carbon atoms; and n is 2, 3 or 4;
or of an alkyl sulfonate salt of the formula $$R^1SO_3M \qquad \text{III}$$

wherein $R^1$ is straight or branched alkyl of from 11–16 carbon atoms; and M is a pharmaceutically acceptable non-toxic cation; by means of a biologically compatible prolonged release carrier therefor whereby the compound is transported into the uterine fluids with sperm during or after coitus.

2. A method as defined in claim 1 wherein R or $R^2$ is $C_{11}$–$C_{30}$ straight chain alkyl.

3. A method as defined in claim 2 where R is $C_{11}$–$C_{20}$ straight chain alkyl.

4. A method as defined in claim 3 wherein M is sodium.

5. A method as defined in claim 3 wherein R is n-tetradecyl.

6. A method as defined in claim 5 wherein M is sodium.

7. A method according to claim 1 in which the prolonged release carrier is a pre-formed polyether-based polyurethane article.

8. A method as defined in claim 3 wherein R is 2-tetradecyl, 4-tetradecyl, 6-tetradecyl, 7-tetradecyl, 7-hexadecyl, 8-hexadecyl, or 9-octadecyl.

9. A method as defined in claim 8 wherein M is sodium.

* * * * *